(12) United States Patent
Kishida et al.

(10) Patent No.: US 7,732,217 B2
(45) Date of Patent: Jun. 8, 2010

(54) APPARATUS AND METHOD FOR READING FLUORESCENCE FROM BEAD ARRAYS

(75) Inventors: Hiroshi Kishida, Tokyo (JP); Masaomi Uchida, Tokyo (JP)

(73) Assignee: Hitachi Software Engineering Co., Ltd., Tokyo (JP)

( * ) Notice: Subject to any disclaimer, the term of this patent is extended or adjusted under 35 U.S.C. 154(b) by 894 days.

(21) Appl. No.: 11/440,082

(22) Filed: May 25, 2006

(65) Prior Publication Data

US 2006/0275891 A1   Dec. 7, 2006

(30) Foreign Application Priority Data

Jun. 3, 2005   (JP)   ............... 2005-164239

(51) Int. Cl.
| | |
|---|---|
| G01N 21/76 | (2006.01) |
| G01B 9/00 | (2006.01) |
| G01J 1/00 | (2006.01) |
| G01J 3/427 | (2006.01) |
| G02B 26/08 | (2006.01) |
| G02B 26/10 | (2006.01) |
| G02B 26/12 | (2006.01) |
| G06K 9/00 | (2006.01) |

(52) U.S. Cl. ............... 436/172; 356/319; 356/123; 356/126; 359/196.1; 388/128

(58) Field of Classification Search ............... None
See application file for complete search history.

(56) References Cited

U.S. PATENT DOCUMENTS 5,922,617 A    7/1999   Wang et al.
6,333,499 B1   12/2001  Sato
6,388,788 B1 * 5/2002   Harris et al. ............ 359/196.1
6,456,734 B1 * 9/2002   Youvan et al. ............ 382/128
7,452,727 B2 * 11/2008  Hennig et al. ............ 436/64
2002/0139936 A1  10/2002  Dumas
2002/0168094 A1 * 11/2002  Kaushikkar et al. ......... 382/128
2003/0030850 A1  2/2003   Heffelfinger
2003/0087282 A1  5/2003   Oshida et al.
2003/0198272 A1  10/2003  Nishioka

FOREIGN PATENT DOCUMENTS

| EP | 1 510 819 A1 | 3/2005 |
| JP | 10-309281 | 11/1998 |
| JP | 2003-156442 | 5/2003 |
| JP | 2004-226234 | 8/2004 |
| JP | 2005-062515 | 3/2005 |

* cited by examiner

*Primary Examiner*—Mark L Shibuya
*Assistant Examiner*—Leon Y. Lum
(74) *Attorney, Agent, or Firm*—Brundidge & Stanger, P.C.

(57) ABSTRACT

When detecting fluorescence of a bead chip array, reflected light from a bead is detected at the same time, so as to recognize the bead position. The reflected light can be detected in a similar manner for all beads, regardless of the presence or absence of a fluorescent substance. If the positions of all beads are detected, accurate detection can be achieved by quantifying only the fluorescence at the detected positions. The fluorescence wavelength alone is detected by a first detector using a wavelength selection filter. Other wavelengths are detected by a second detector, thereby obtaining the reflected light. Data on the reflected light is processed into an image for obtaining the bead profile, the bead position is recognized by detecting the center position based on the profile, and the fluorescence is quantified based on the bead position.

1 Claim, 6 Drawing Sheets

APPARATUS AND METHOD FOR READING FLUORESCENCE FROM BEAD ARRAYS

BACKGROUND OF THE INVENTION

1. Field of the Invention

The present invention relates to fluorescence image acquisition in the field of life science. In particular, it is suitable for the accurate detection of fluorescence from bead arrays.

2. Background Art

Conventionally, fluorescence image acquisition in the field of life science is performed using apparatuses for detecting fluorescent substances on a planar chip, typically a DNA chip. Such an apparatus reads spots that are two-dimensionally arranged and is configured with array form information in advance. Overall positions of the spots are determined based on the array form information and compared with fluorescence information, and a detection matrix is aligned with individual spots.

For example, JP Patent Publication (Kokai) No. 2004-226234 A below discloses a bead-reading method and apparatus in which a functional bead having a coating layer on the surface thereof in which nanoparticles exist is introduced into a flow passage. A voltage is applied to the functional bead in the flow passage so as to cause it to emit light having a wavelength specific to the nanoparticle. The functional bead is then identified based on light emission. In this case, a prerequisite is that the array form information of the beads is obtained in advance.

SUMMARY OF THE INVENTION

However, because the above technology is based on the array form information identified in advance, it is not effective when the array form of the beads when arrayed differ from the array form when detected, or for beads whose array form information cannot be obtained. Specifically, in bead chip arrays, since a glass bead has a diameter of 100 μm relative to the groove width of 130 μm, it is difficult to control the behavior of the beads, and the beads might be arranged in a zigzag pattern or lopsided to either wall surface. Also, in a reaction process prior to detection, because a solution of test substance is sent to and from the array portion, the beads can move in a little gap or at an array portion lopsided to a wall surface, resulting in an array form different from that as originally arrayed. Consequently, even if the array form information is provided in advance, the actual position of the array could be different when detected. Thus, accurate detection is difficult with the conventional method. While obtained fluorescence is used for detecting the position of the beads, fluorescence can be very small in some cases in expression analysis. In such cases, even the presence or absence of a bead may not be detectable, which makes it impossible to apply the method to the bead chip array in which inspection items are managed based on the array sequence.

It is an object of the invention to automatically recognize the position of beads and to accurately detect the fluorescence therefrom.

In order to achieve the above object, the position of beads is recognized by detecting reflected light from the bead simultaneously with the detection of fluorescence therefrom.

Reflected light can be detected in a similar manner for all beads, regardless of the presence or absence of a fluorescent substance. If the positions of all the beads are detected, accurate detection can be achieved by quantifying the fluorescence at the detected positions alone. Thus, in accordance with the invention, a fluorescent substance is caused to emit fluorescence with a light source having the absorption wavelength of the fluorescent substance, and only the fluorescence wavelength is detected with a first detector together with a wavelength selection filter. Wavelengths other than the fluorescence wavelength are detected with a second detector so as to obtain reflected light. The data of the reflected light is subjected to image processing so as to obtain the profile of the bead. The center position of the bead is detected based on the profile so as to recognize the position of the bead and then the fluorescence is quantified based on the position of the bead.

According to the invention, bead recognition can be achieved under any conditions by using a reflection image as additional means, without relying on a fluorescence image for recognizing the position of beads. In this way, the position of beads can be accurately obtained. By detecting fluorescence with reference to the accurate bead position, fluorescence from each bead can be accurately detected.

Because the position of beads is automatically detected, array form information does not need to be inputted in advance and input error can be eliminated, thereby further improving the accuracy of fluorescence detection.

Even when the form as originally arrayed is zigzagged or lopsided and individual bead arrays differ from one another in these respects, fluorescence from each bead can be accurately detected by obtaining fluorescence with respect to the accurate position of the bead.

DESCRIPTION OF PREFERRED EMBODIMENTS OF THE INVENTION

Hereafter, an embodiment of the invention will be explained in detail with reference to the drawings.

Figure 1:
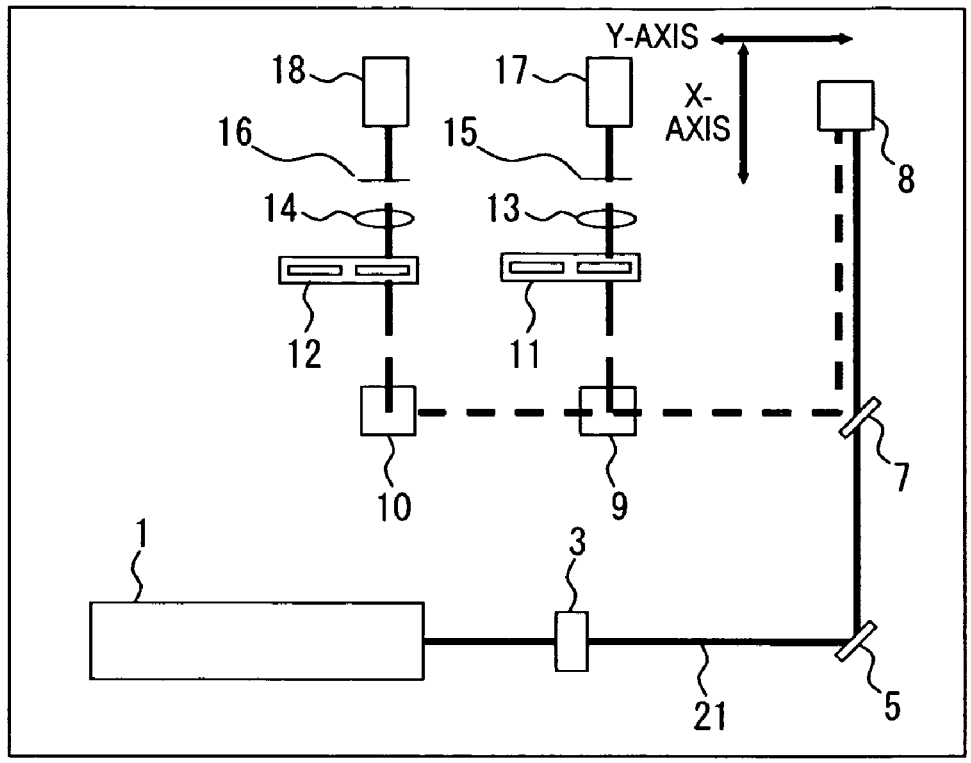
FIG. 1 shows a top view of a block diagram of an optical configuration of an apparatus for reading fluorescence from a bead array according to an embodiment of the invention.
Figure 2:
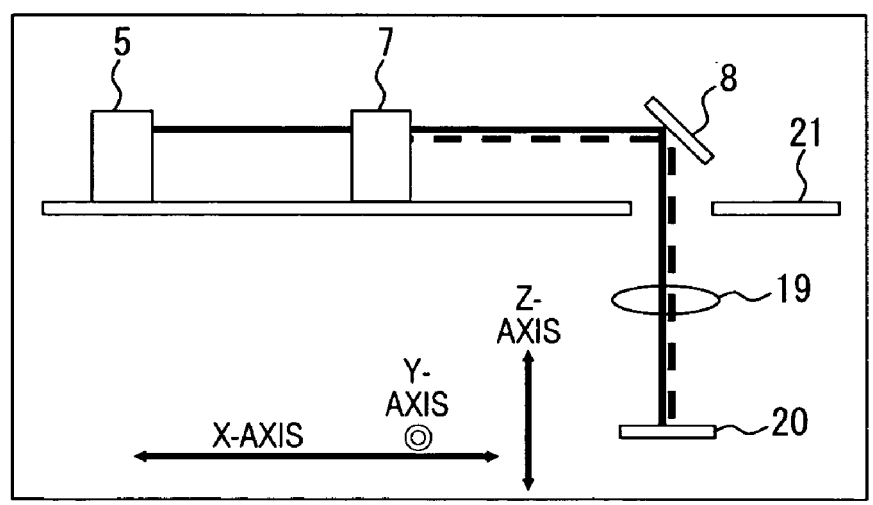
FIG. 2 shows a side view of the block diagram of the optical configuration of the apparatus for reading fluorescence from bead arrays.

FIGS. 1 and 2 show block diagrams of an optical configuration of an apparatus for reading fluorescence from bead arrays according to an embodiment of the invention.

The apparatus for reading fluorescence from bead arrays, as shown in FIG. 1, includes: a fluorescence excitation light source 1; a beam expander 3 for converting a beam irradiated from the fluorescence excitation light source 1 into an appropriate beam width; a mirror 5 for guiding an optical path; a mirror 8 for bending the beam in the direction of an object 20 to be measured; a pupil lens 19 for focusing the beam on the object 20 to be measured; a perforated mirror 7 for guiding a returning light from the object 20 to be measured to a light-receiving system; a first dichroic mirror 9 for selectively separating and reflecting the fluorescent light from the object to be measured; a wavelength selection filter 11 for selecting the wavelength of the fluorescent light; an image-forming lens 13 for forming an image of the fluorescent light on a first photoreceiver (detector) 17; a pinhole 15 for narrowing focal depth; a second dichroic mirror 10 for selectively separating wavelengths other than that of the fluorescent light so as to receive the reflected light from the object 20 to be measured; a second wavelength selection filter 12 for selecting wavelengths other than that of the fluorescent light; an image-forming lens 14 for forming an image of wavelengths other than that of the fluorescent light on a second photoreceiver (detector) 18; a pinhole 16 for narrowing focal depth; and an optical plate 21 for mounting the optical system.

Figure 3:
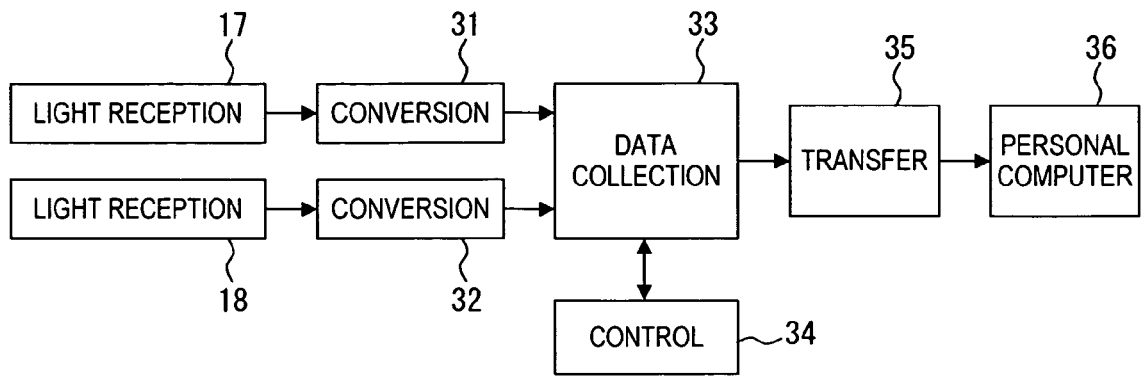
FIG. 3 shows a block diagram of a signal control structure of the apparatus for reading fluorescence from bead arrays.

FIG. 3 shows a block diagram of a data processing system to which the optical system is connected. An electric signal of the fluorescent light received by the first photoreceiver 17 is converted into a digital signal by a conversion means 31. Similarly, an electric signal of optical components that have wavelengths other than that of the fluorescent light and that are received by the second photoreceiver 18 is converted into a digital signal by a conversion means 32. The converted digital signals are stored in a data collecting means 33 and sent to a computer 36 by a transfer means 35.

In accordance with the foregoing configuration, the fluorescent substance of the object 20 to be measured is excited by a beam irradiated from the excitation light source 1 that has passed through an appropriate beam expander 3, mirror 5, mirror 7, and mirror 8. The fluorescent light is collected by the pupil lens 19 and sent to the light-receiving system by the mirror 7. The mirror 7 is a perforated mirror and the excitation light passes through an opening therein. Because the light irradiated in all directions is collected by the pupil lens, the light from the object 20 to be measured has a beam width wider than the excitation light, and it is reflected by the reflecting surface of the mirror 7 to the light receiving system. The light from the object to be measured includes not only the fluorescent light but also the reflected light of the excitation light. The mirror 7 also sends the reflected light to the light-receiving system. In the light-receiving system, the fluorescent light is selectively separated by the dichroic mirror 9, and it is passed through the first wavelength selection filter 11, so as to increase the purity thereof. Then, an image is formed by the image-forming lens 13, and components other than those at the focal position are removed by the pinhole 15. The fluorescent light is then converted into an electric signal by the first photoreceiver 17. The reflected light components other than the fluorescent light that are obtained by the mirror 7 pass through the second dichroic mirror 10 and they also pass through the second wavelength selection filter 12 so as to remove the fluorescent light component. Then, an image is formed by the second image-forming lens 14, and components other than those at the focal position are removed by the second pinhole 16. The resultant light is converted into an electric signal by the second photoreceiver 18. The fluorescent light component and the reflected light component converted into electric signals by the first and second photoreceivers 17 and 18 are each converted into digital signals by a first and second conversion means. A 16-bit A/D converter may be employed for the conversion means. An amplifier or the like may be added to the input side of the A/D converter such that a signal amplitude commensurate with the input of the A/D converter can be obtained. While the quantization number of the A/D converter is 16 bits in the embodiment, other bit numbers may be applicable. When the quantization number is increased, reduction in quantization noise can be expected. The digitized fluorescent light component and reflected light component are sent to the data collecting unit 33 that includes a shift register and a memory, where they are temporarily stored as data. The input/output timing and the like of the data collecting unit 33, and the conversion means 31 and 32 are controlled by a control means 34. A transfer means 35 outputs data to the computer 36 via the control means 34. While a 16-bit parallel system is employed for data output, it is appropriate to employ a packet system LAN (local area network) or USB (universal serial bus) system for faster data transfer.

In accordance with the above configuration, the fluorescent light and reflected light from an object to be measured can be digitized and fed into a computer.

Figure 4:
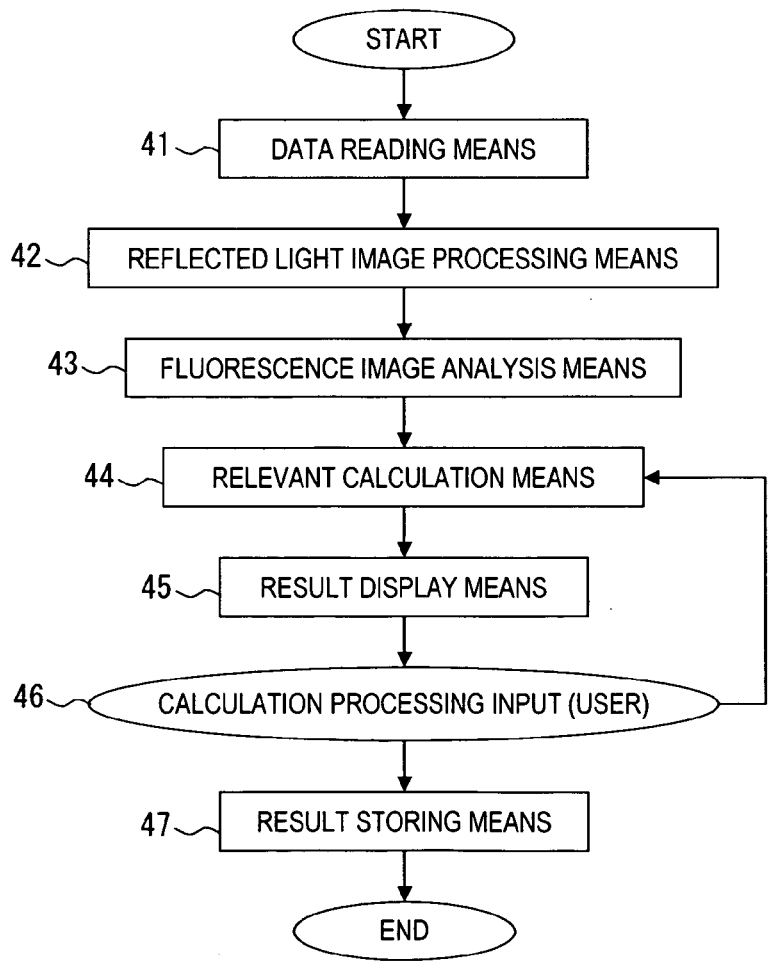
FIG. 4 schematically shows a flow chart of a software program of the apparatus for reading fluorescence from bead arrays.

FIG. 4 schematically shows the flow of an algorithm for recognizing each bead of the object to be measured from the data of fluorescent light and reflected light fed into the computer, calculating a center position, obtaining array form information, and calculating a fluorescence image. The algorithm includes: means 41 for reading files of the fluorescent light and reflected light data into an application; a reflection image processing means 42 for recognizing the bead through image processing from the data of the reflected light component that has been read, calculating a center position, and obtaining array form information; a fluorescence image analysis means 43 for analyzing the fluorescence quantity of the bead based on the array form information; an arithmetic processing input means 46 via which a user designates a method for analyzing the fluorescence quantity; a calculation means 44 for analyzing the fluorescence quantity based on the analysis method; a result display means 45 for displaying the result of calculation on a monitor; and means 47 for storing the result.

In the invention, it is particularly worth noting that the bead position information is obtained with the use of reflected light, and fluorescence quantity is quantified based on the information. The reflection image processing means 42 will be described in detail with reference to FIGS. 5 to 7.

Figure 5:
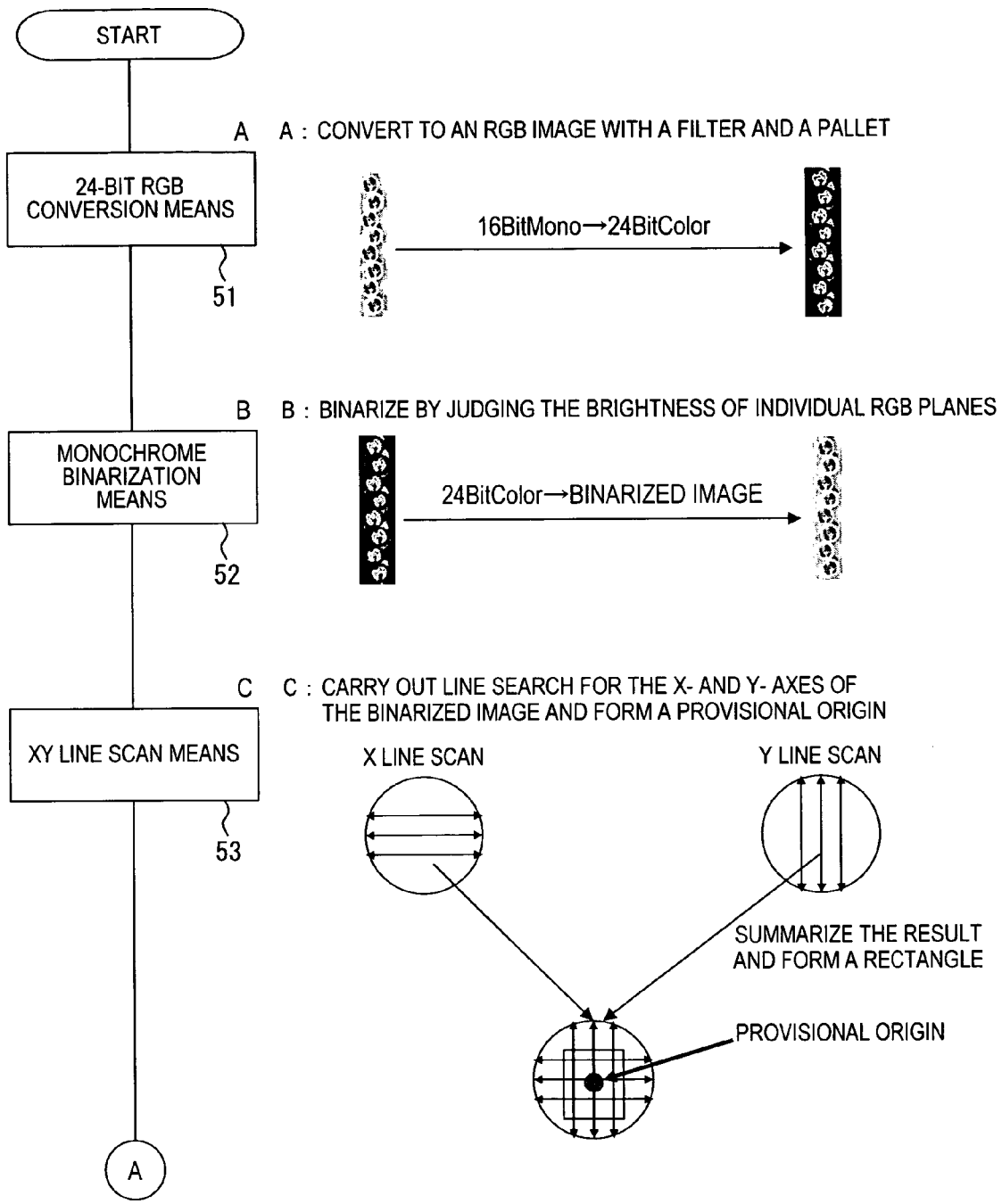
FIG. 5 shows a detailed flow chart (1) of the software for detecting bead positions.

In the reflection image processing means 42, 16-bit monaural data of reflected light components is converted into 24-bit RGB color data in a 24-bit RGB conversion process 51. This is for the purpose of adding color temperature information to the monaural shades (brightness). A threshold value is set with respect to the color temperature information, and the data is binarized in a monochrome binarization process 52 with respect to the threshold value. Line search is carried out on the x- and y-axes of the binarized image file by an xy line scan means 53, and the center of the lines where x axis and y axis intersect is designated as a provisional origin (FIG. 5).

Figure 6:
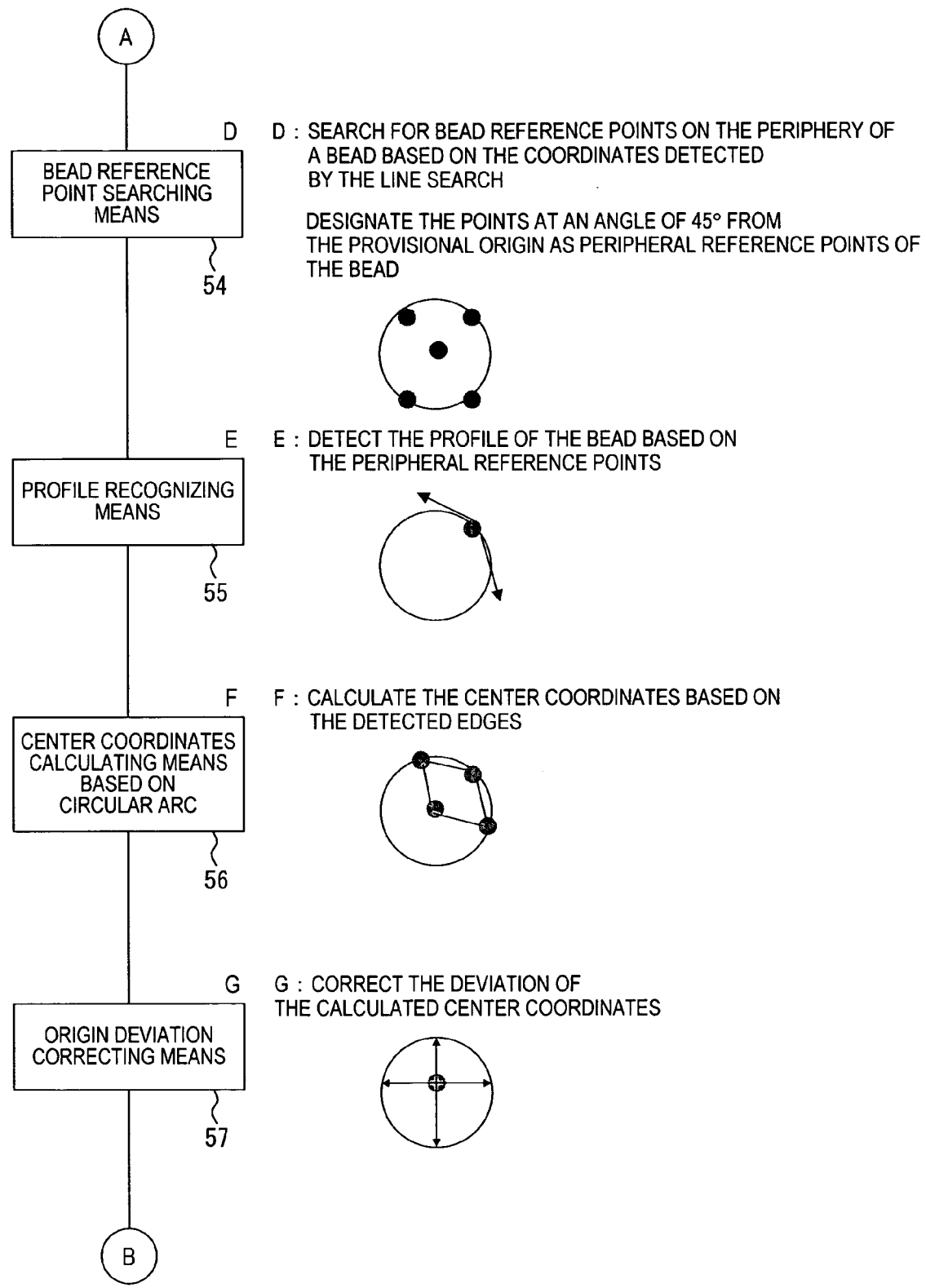
FIG. 6 shows a detailed flow chart (2) of the software for detecting bead positions.

Thereafter, in a bead reference point search means 54, the four points that are at an angle of 45° from the provisional origin are designated as peripheral reference points. A profile recognizing means 55 then recognizes the profile of the bead based on the peripheral reference points, and a center coordinate calculating means 56 calculates the center coordinates based on the profile obtained by the profile recognizing means 55. Since the accurate center position of the bead is not yet obtained at this point, alignment between the external size (100 μm) of the bead and the profile is sought by an origin deviation correcting means 57, so as to correct the position to the accurate center position (FIG. 6).

Figure 7:
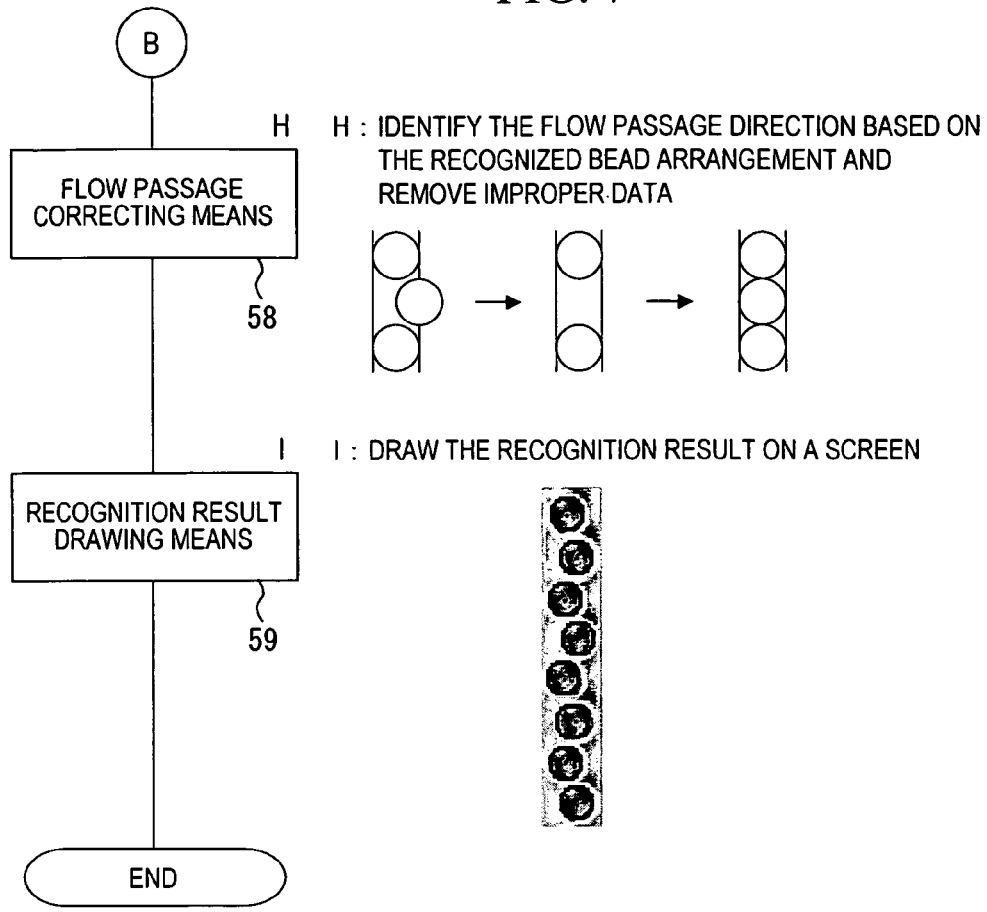
FIG. 7 shows a detailed flow chart (3) of the software for detecting bead positions.

A flow passage correcting means 58 is used for eliminating from the recognized bead arrangement information (center position information) certain improper data such as, for example, data of a bead deviating in the direction of the groove (flow passage). Finally, the recognition result is displayed on the monitor using a recognition result drawing means 59, thereby enabling the recognition of the center position of each bead and obtaining information about the array form on the bead chip plate. Once the array form information is obtained, the fluorescence quantity can be quantified with the use of an existing fluorescence image recognition means (FIG. 7).

Figure 8:
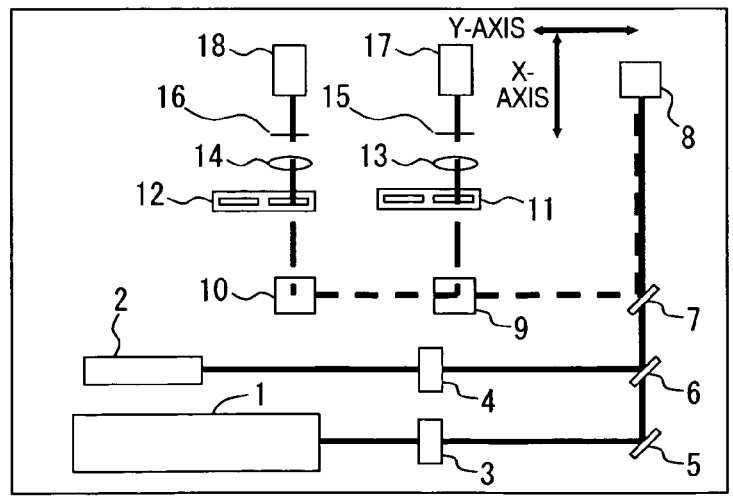
FIG. 8 shows a block diagram of an optical configuration of an apparatus for reading fluorescence from bead arrays according to another embodiment of the invention.
Figure 9:
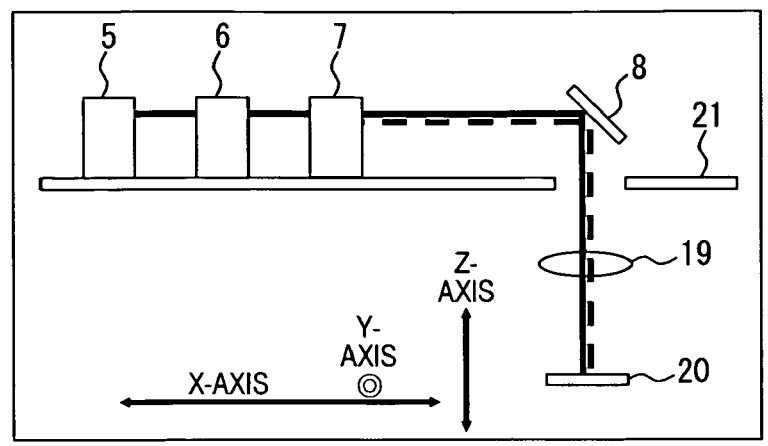
FIG. 9 shows a block diagram of an optical configuration of an apparatus for reading fluorescence from bead arrays according to another embodiment of the invention.

FIGS. 8 and 9 show another embodiment. In addition to the configuration shown in FIGS. 1 and 2, the present configuration includes a second excitation light source 2, a second beam expander 4, and a mirror 6 for guiding a second excitation light to the same axis of the first excitation light path. In this configuration, the second excitation light source 2 is dedicated for the reflected light so as to actively acquire it.

Figure 10:
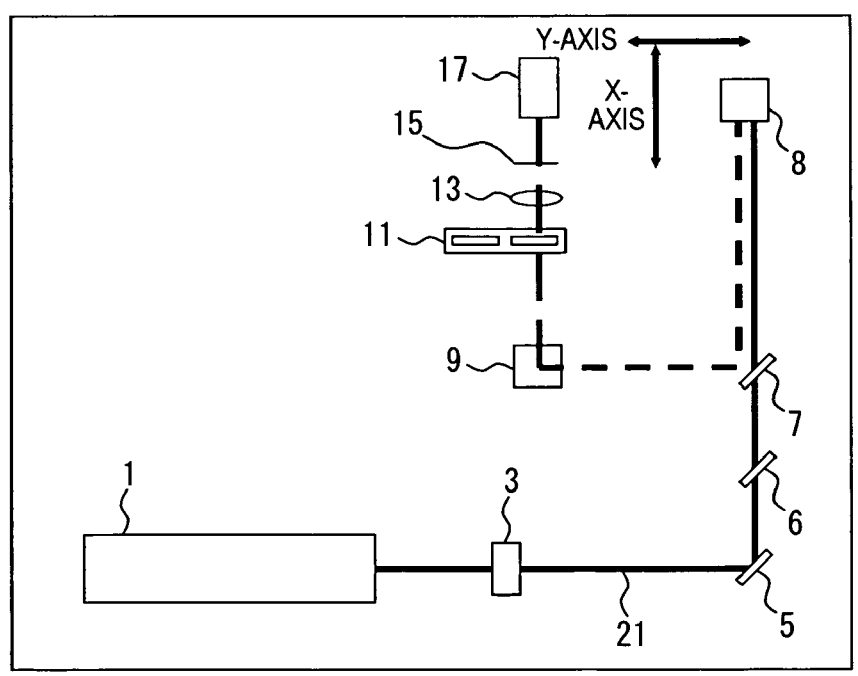
FIG. 10 shows a block diagram of an optical configuration of an apparatus for reading fluorescence from bead arrays according to another embodiment of the invention.

FIG. 10 shows a configuration which differs from the configuration of FIG. 1 in that it lacks the second dichroic mirror 10 for selectively separating wavelengths other than that of the fluorescent light so as to receive the reflected light from the object 20 to be measured, the second wavelength selection filter 12 for selecting wavelengths other than that of the fluorescent light, the image-forming lens 14 for forming an image of wavelengths other than that of the fluorescent light on the second photoreceiver 18, and the pinhole 16 for narrowing focal depth, and in that the first wavelength selection filter 11 is made removable. This configuration may be applicable when employing a method for obtaining the reflected light and fluorescent light sequentially rather than simultaneously. This configuration requires less components yet provides the same effects at reduced cost.

What is claimed is:

1. A method for reading fluorescence from a bead array for acquiring a fluorescence image of a bead chip array in which beads are arrayed in a groove formed in a resin, the method comprising:
    causing an excitation light source to emit an excitation light to a bead to which is attached a fluorescent substance having an absorption wavelength contained in the excitation light, wherein light from the bead has a fluorescence component having a fluorescence wavelength resulting from excitation of the fluorescent substance with the excitation light, and a reflection component resulting from reflection of the excitation light from the bead;
    separating, from the light from the bead, first light containing substantially the fluorescence component with a first dichroic mirror for selectively separating and reflecting the fluorescent light from the bead;
    converting the first light into electric signals by a first photoreceiver;
    converting the electric signals obtained from the first light into digital signals by a first conversion means to obtain first digitized data of said fluorescence component;
    obtaining, from the light from the bead, second light containing substantially the wavelengths other than the fluorescence wavelength with a second dichroic mirror for selectively separating wavelengths other than that of the fluorescent light so as to receive the reflected light from the bead;
    converting the light having wavelengths other than the fluorescence wavelength into electric signals by a second photoreceiver;
    converting the electric signals obtained from the light having wavelengths other than the fluorescence wavelength into digital signals by a second conversion means to obtain second digitized data of said reflection component;
    feeding the first and second digitized data into a computer;
    recognizing the bead through image processing of the second digitized data, calculating a center position thereof, and obtaining array form information by a reflection image processing means, and
    analyzing the fluorescence quantity of the bead by a fluorescence image analysis means based on the array form information,
    wherein the method is performed for each bead in the bead array, and
    wherein the calculation of center position is conducted by
    converting two-dimensional 16-bit monaural data of reflection components into 24-bit RGB color data by a 24-bit RGB conversion process in order to add color temperature information to monaural shades of the monaural data;
    setting a threshold value with respect to the color temperature information, binarizing the threshold value by a monochrome binarization process to obtain a two-dimensional binarized image file;
    carrying out a line search on x and y axes of the binarized image file, designating a center of the lines where the x axis and the y axis intersect as a provisional origin;
    designating four points that are at an angle of 45° respectively from each of the positive and negative x and y axes, referenced to the provisional origin, as peripheral reference points;
    recognizing a profile of the bead based on the peripheral reference points;
    calculating the center coordinates based on the recognized profile; and
    seeking alignment between an external size of the bead and the profile to obtain an accurate center position.

\* \* \* \* \*